United States Patent
Beveridge et al.

(10) Patent No.: US 12,390,172 B2
(45) Date of Patent: Aug. 19, 2025

(54) METHOD AND APPARATUS FOR DISPLAYING MEDICAL IMAGES

(71) Applicant: CANON MEDICAL SYSTEMS CORPORATION, Otawara (JP)

(72) Inventors: Erin Beveridge, Edinburgh (GB); Brian Mohr, Edinburgh (GB); Naotaka Sakashita, Utsunomiya (JP); Ryo Okuda, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1150 days.

(21) Appl. No.: 17/180,098

(22) Filed: Feb. 19, 2021

(65) Prior Publication Data

US 2022/0265183 A1  Aug. 25, 2022

(51) Int. Cl.
| | | |
|---|---|---|
| A61B 6/03 | (2006.01) | |
| A61B 5/00 | (2006.01) | |
| A61B 6/00 | (2024.01) | |
| A61B 6/46 | (2024.01) | |
| A61B 6/50 | (2024.01) | |
| G16H 30/40 | (2018.01) | |

(52) U.S. Cl.
CPC ............. *A61B 6/032* (2013.01); *A61B 5/742* (2013.01); *A61B 6/467* (2013.01); *G16H 30/40* (2018.01); *A61B 6/463* (2013.01); *A61B 6/481* (2013.01); *A61B 6/504* (2013.01)

(58) Field of Classification Search
CPC ......... A61B 6/032; A61B 5/742; A61B 6/467; A61B 6/463; A61B 6/481; A61B 6/504; G16H 30/40
See application file for complete search history.

(56) References Cited

U.S. PATENT DOCUMENTS

| 9,159,127 B2 | 10/2015 | Meetz et al. |
| 10,489,628 B2 | 11/2019 | Liu et al. |
| 2016/0242638 A1 | 8/2016 | Durbin et al. |
| 2017/0172408 A1 | 6/2017 | Samadani et al. |
| 2017/0367633 A1 | 12/2017 | Samadani |
| 2018/0168444 A1 | 6/2018 | Foss |

(Continued)

FOREIGN PATENT DOCUMENTS

| JP | 2010-530270 A | 9/2010 |
| JP | 2016-523632 A | 8/2016 |

(Continued)

OTHER PUBLICATIONS

Mokli, Y., et al., "Computer-aided imaging analysis in acute ischemic stroke—background and clinical applications," Neurological Research and Practice. vol. 1(23), 2019. p. 1-13 (Year: 2019).*

(Continued)

*Primary Examiner* — Sean A Frith
(74) *Attorney, Agent, or Firm* — Oblon, McClelland, Maier & Neustadt, L.L.P.

(57) ABSTRACT

An image display apparatus comprises processing circuitry configured to receive medical image data including a representation of at least one eye of a subject, process the medical image data to determine an eye gaze direction for the at least one eye of the subject, and select a display mode for displaying the medical image data in dependence on the determined eye gaze direction.

24 Claims, 8 Drawing Sheets

(56) References Cited

U.S. PATENT DOCUMENTS

| | | | | |
|---|---|---|---|---|
| 2018/0177446 | A1* | 6/2018 | Okabe | G16H 30/20 |
| 2018/0268737 | A1* | 9/2018 | Garnavi | G06N 3/084 |
| 2019/0046124 | A1 | 2/2019 | Samadani | |
| 2019/0150732 | A1 | 5/2019 | Samadani et al. | |
| 2019/0192089 | A1 | 6/2019 | Maresky et al. | |
| 2019/0272636 | A1 | 9/2019 | Mansi et al. | |
| 2020/0337554 | A1* | 10/2020 | Shin | A61B 5/00 |
| 2020/0350075 | A1* | 11/2020 | Noch | G10L 25/66 |
| 2020/0359981 | A1* | 11/2020 | Straka | G16H 50/20 |

FOREIGN PATENT DOCUMENTS

| | | |
|---|---|---|
| JP | 2016-523635 A | 8/2016 |
| JP | 2017-529891 A | 10/2017 |
| JP | 2021-20054 A | 2/2021 |
| UA | 73957 U | 10/2012 |
| WO | WO 2017/106645 A1 | 6/2017 |

OTHER PUBLICATIONS

Brainomix, e-aspects https://brainomix.com/e-aspects, retrieved on May 20, 2019, 9 pages.

Kobayashi, M., "Horizontal gaze deviation on computed tomography: the visual criterion and lesion characteristics in ischemic stroke," Acta Neurol Belg, vol. 118, No. 581. https:/doi.org/10.1007/s13760-018-0949-1, 2018, 7 pages.

Spokoyny, I. et al., "Visual Determination of Conjugate Eye Deviation on Computed Tomography Scan Predicts Diagnosis of Stroke Code Patients," Journal of Stroke and Cerebrovascular Diseases, vol. 25, No. 12, Dec. 2016, 5 pages.

Girshick, R. et al., "Rich feature hierarchies for accurate object detection and semantic segmentation", The IEEE Conference on Computer Vision and Pattern Recognition (CVPR), Jun. 2014, 8 pages.

Lyden, P et al., "NIH Stroke Scale/Score (NIHSS) Calculates the NIH Stroke Scale for quantifying stroke severity," National Institutes of Health Stroke Scale/Score (NIHSS), https://www.mdcalc.com/nihstroke-scale-score-nihss, 7 pages.

Gaillard, F. et al., "Prévost sign (eyes)," https://radiopaedia.org/articles/prevost-sign-eyes?lang=gb, 5 pages.

"New results demonstrate ability to automatically detect suspected large-vessel occlusion stroke in non-contrast CT head scans," Neuro News International, https://neuronewsinternational.com/automatically-detect-lvo-stroke/, Nov. 16, 2018, 2 pages.

Chung, C. Y. et al., "Automated Detection of Hyperdense MCA Sign And Notification of Large Vessel Occlusion Using Artificial Intelligence," SVIN 11$^{th}$ Annual Meeting, Nov. 14-17, 2018, 1 page.

Attenhofer, K. S. et al., "The Sustained DeyeCOM Sign As a Predictor of Large Vessel Occlusions and Stroke Mimics," J. Stroke Cerebrovasc Dis., vol. 27, No. 6, Jun. 2018, 9 pages.

Lisowska, A. et al., "Thrombus Detection in CT Brain Scans using a Convolutional Neural Network," In Proceedings of the 10th International Joint Conference on Biomedical Engineering Systems and Technologies, DOI: 10.5220/0006114600240033, 2017, 10 pages.

Office Action issued Jan. 28, 2025, in corresponding Japanese Patent Application No. 2021-113558, 3 pages.

\* cited by examiner

METHOD AND APPARATUS FOR DISPLAYING MEDICAL IMAGES

FIELD

Embodiments described herein relate generally to a method and apparatus for displaying medical images, for example images of a patient with suspected stroke.

BACKGROUND

A stroke may be an example of a serious life-threatening medical condition and may require urgent medical attention. Typically, a non-contrast CT scan (NCCT) may be performed as a first line in stroke diagnosis. The NCCT scan results may be used to exclude hemorrhagic stroke as a cause. The NCCT scan results may be used to exclude conditions that mimic the symptoms of stroke, for example seizure and brain tumor. The NCCT scan results may be used to identify dense vessels, which may be indicative of a clot, and/or to identify ischemia.

A subsequent CT angiography (CTA) that combines a CT scan with an injection of a contrast medium may be performed to confirm an initial diagnosis and/or to gain more information to aid a treatment decision.

One cause of ischemic stroke may be the presence of a large vessel occlusion. Large vessel occlusions are acute blockages of the anterior and posterior circulation.

If a large vessel occlusion is present in a patient, thrombectomy may be an appropriate treatment. Mechanical thrombectomy aims to restore blood flow by removing an obstructing blood clot using a clot retrieval device delivered via an intravascular catheter. To receive thrombectomy treatment, a patient may need to be transferred to a hospital which is capable of performing thrombectomy. The process of determining that a large vessel occlusion is present and that thrombectomy is indicated may be time critical.

Determining which patients may have a large vessel occlusion and may be eligible for potentially life-saving thrombectomy treatment may form a key part of stroke clinical workflows. Evidence of the benefits of endovascular thrombectomy is driving a need for rapid identification of potentially eligible patients.

Determining whether a patient has a large vessel occlusion typically requires an intracranial vascular imaging study, according to American Heart Association (AHA) guidelines. There are several challenges that may be associated with this. There may be a lack of expertise available to read the vascular studies. There may be issues with the timing of a contrast agent, which may lead to non-diagnostic studies. Some patients have contraindications to iodinated contrast agents that are used in vascular studies. Not all hospitals perform intracranial vascular studies routinely.

The presence of certain imaging features in non-contrast studies may indicate that an occlusion is present. The indication that the occlusion is present may have high specificity but low sensitivity. One such imaging feature is a hyper-dense artery sign (HAS) in non-contrast computed tomography (CCT). Another such imaging feature is a susceptibility vessel sign (SVS) on a T2* gradient recalled echo (GRE) magnetic resonance study (MRI).

Clinical triage scales may be used to indicate whether an large vessel occlusion is present. Examples of clinical scales that may be used for LVO triage include the Rapid Arterial oCclusion Evaluation (RACE) scale and the Cincinnati Prehospital Stroke Scale.

Studies have identified that eye deviation may identify patients who are likely to have large vessel occlusion. Eye deviation is included as a component in most clinical scales that are used for LVO triage (for example, RACE and Cincinnati).

In some circumstances, non-contrast imaging features or clinical triage scales may not be sensitive and specific enough to identify all potentially eligible thrombectomy candidates.

Some currently available LVO triage methods identify CTA studies in which potential LVOs are present. In such currently available LVO triage methods, LVO is indicated directly.

BRIEF DESCRIPTION OF THE DRAWINGS

Embodiments are now described, by way of non-limiting example, and are illustrated in the following figures, in which.

DETAILED DESCRIPTION

Certain embodiments provide an image display apparatus comprising processing circuitry configured to: receive medical image data including a representation of at least one eye of a subject; process the medical image data to determine an eye gaze direction for the at least one eye of the subject; and select a display mode for displaying the medical image data in dependence on the determined eye gaze direction.

Certain embodiments provide a method comprising: receiving medical image data including a representation of at least one eye of a subject; processing the medical image data to determine an eye gaze direction for the at least one eye of the subject; and selecting a display mode for displaying the medical image data in dependence on the determined eye gaze direction.

Figure 1:
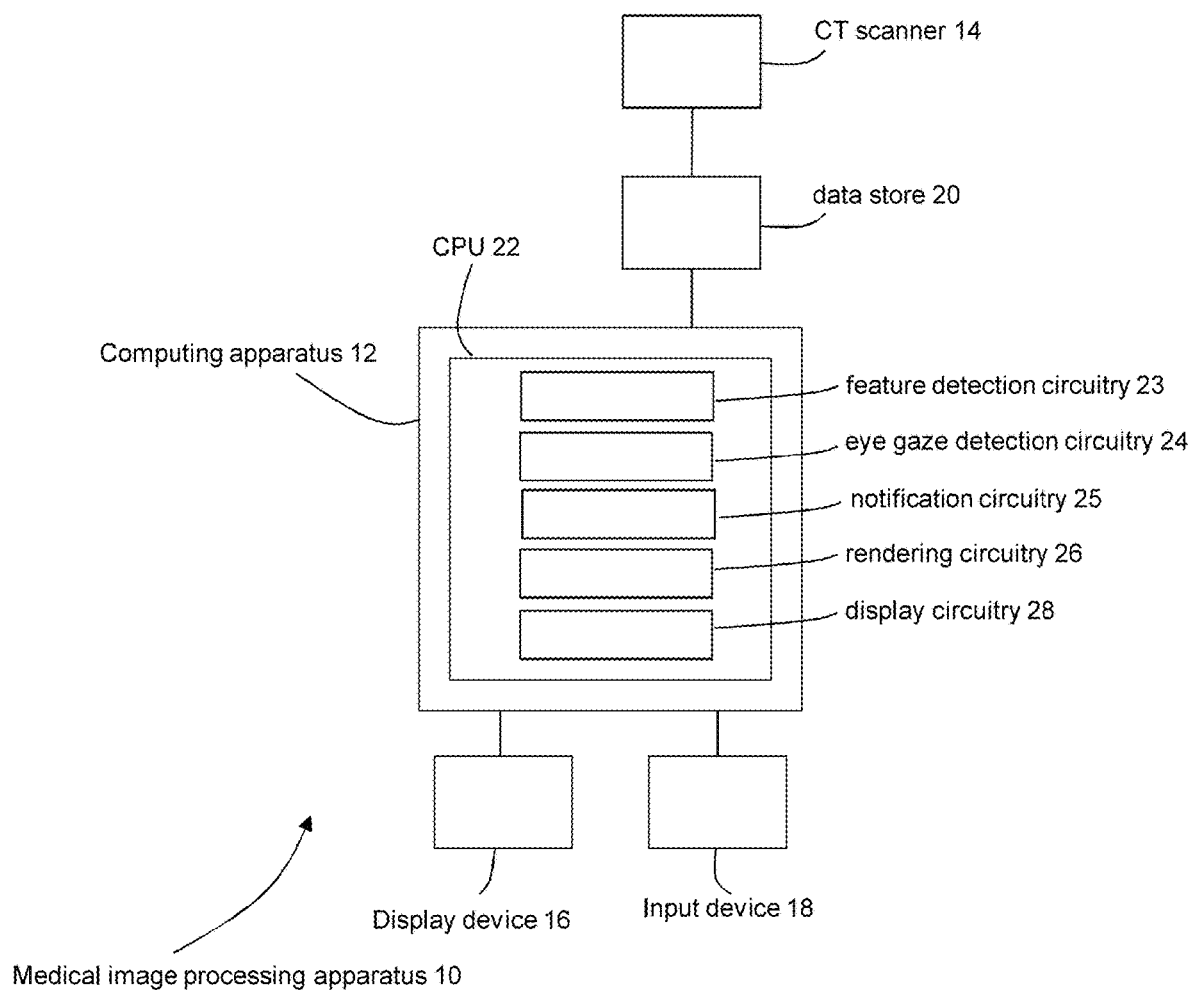
FIG. 1 is a schematic diagram of an apparatus according to an embodiment.

A medical image processing apparatus 10 according to an embodiment is illustrated schematically in FIG. 1. The medical image processing apparatus 10 is configured to process and display medical images of a patient or other subject. The medical image processing apparatus 10 may also be referred to as an image display apparatus or image displaying apparatus.

The medical image processing apparatus 10 comprises a computing apparatus 12, which in this case is a personal computer (PC) or workstation. The computing apparatus 12 is connected to a display device 16, for example a screen, and an input device or devices 18, such as a computer keyboard and mouse. In some embodiments, the display device 16 is a touch screen, which also acts as an input device 18. The computing apparatus 12 is connected to a data store 20.

The medical image processing apparatus 10 is connected to a CT scanner 14 which is configured to perform a non-contrast CT scan (NCCT) scan and a CT angiography (CTA) scan of a patient or other subject to obtain volumetric medical imaging data. In the present embodiment, each scan comprises a scan of the brain. In other embodiments, any suitable body part may be scanned.

In alternative embodiments, data may be obtained using any suitable modality and/or acquisition technique. The CT scanner 14 may be replaced or supplemented by one or more scanners configured to obtain two-dimensional or three-dimensional imaging data in any suitable imaging modality, for example a CT scanner, cone-beam CT scanner, MRI (magnetic resonance imaging) scanner, X-ray scanner, ultrasound scanner, PET (positron emission tomography) scanner or SPECT (single photon emission computed tomography) scanner.

Data obtained using the CT scanner 14 is stored in data store 20 and supplied to the computing apparatus 12. In other embodiments, the computing apparatus 12 may obtain the data directly from the CT scanner 14. In alternative embodiments, the medical image processing apparatus 10 receives medical imaging data and/or medical images from one or more further data stores (not shown) instead of or in addition to data store 20. For example, the medical image processing apparatus 10 may receive medical imaging data from one or more remote data stores which may form part of a Picture Archiving and Communication System (PACS) or other information system, for example a laboratory data archive, an Electronic Medical Record (EMR) system, or an Admission Discharge and Transfer (ADT) system.

Computing apparatus 12 comprises a central processing unit (CPU) 22. The computing apparatus 12 provides a processing resource for automatically or semi-automatically processing data sets. In the present embodiment, the data sets comprise medical imaging data.

The computing apparatus 12 includes feature detection circuitry 23 configured to process imaging data to identify one or more imaging features, for example to detect regions of dense vessel; eye gaze detection circuitry 24 configured to determine a direction of eye gaze; notification circuitry 25 configured to flag potential thrombectomy candidates; rendering circuitry 26 configured to render images from imaging data; and display circuitry 28 configured to select and position rendered views on a display screen 16 or on any suitable display.

In the present embodiment, the circuitries 23, 24, 25, 26, 28 are each implemented in computing apparatus 12 by means of a computer program having computer-readable instructions that are executable to perform the method of the embodiment. However, in other embodiments, the various circuitries may be implemented as one or more ASICs (application specific integrated circuits) or FPGAs (field programmable gate arrays). In the present embodiment, the circuitries 23, 24, 25, 26, 28 are each implemented as part of the CPU 22. In alternative embodiments, the circuitries 23, 24, 25, 26, 28 may be implemented separately or form part of two or more CPUs. In further embodiments, at least part of the method may be performed on one or more Graphical Processing Units (GPUs).

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
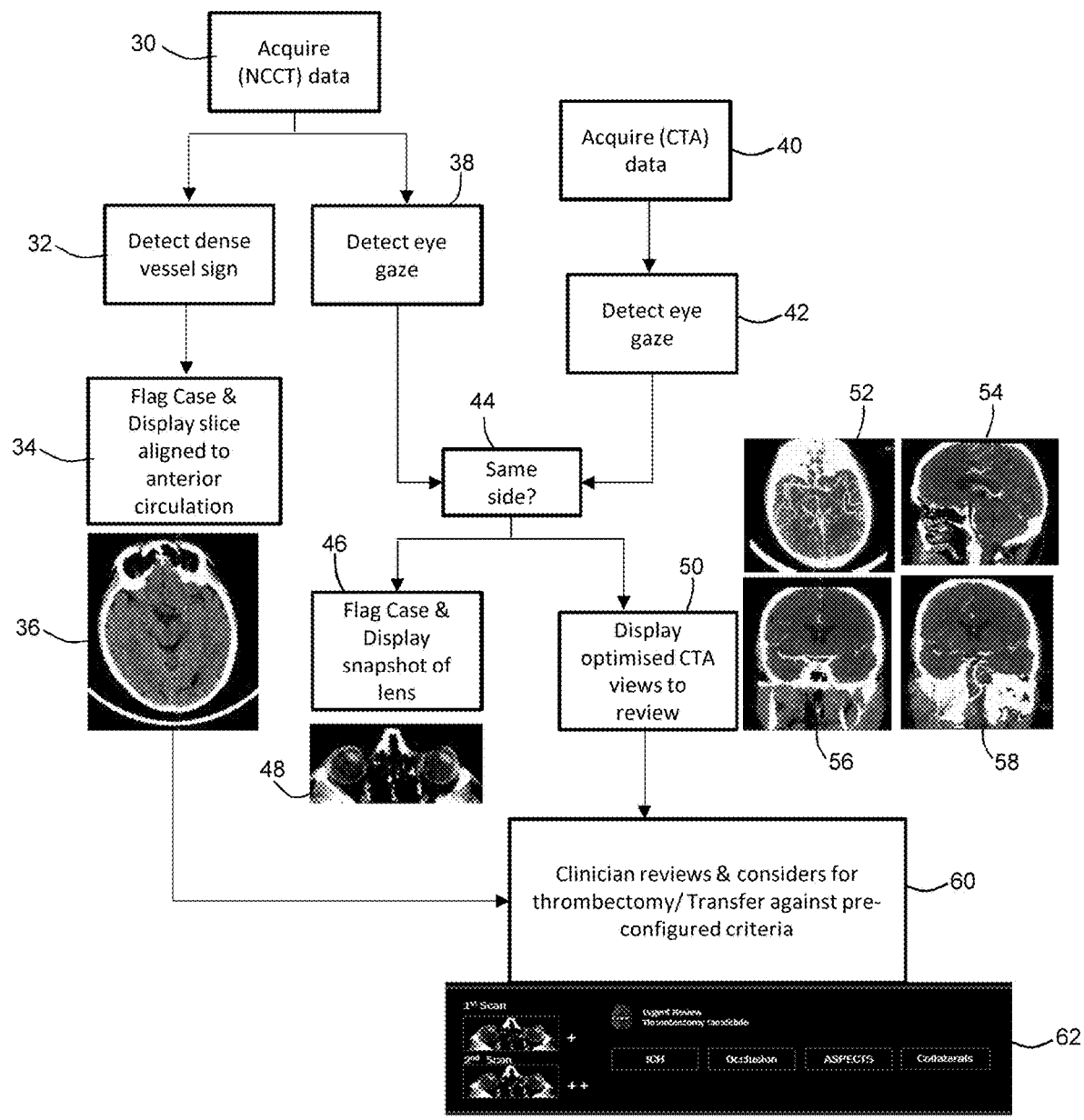
FIG. 2 is a flow chart illustrating in overview a method of an embodiment.

The system of FIG. 1 is configured to perform a series of stages as illustrated in overview in the flow chart of FIG. 2.

At stage 30, the CT scanner acquires a non-contrast CT (NCCT) scan of the brain of a patient who is suspected to have had a stroke. It is normal clinical practice to perform a non-contrast CT scan of the brain when stroke is suspected.

Volumetric data from the NCCT scan is passed to the data store 20, and from the data store 20 to the feature detection circuitry 23 and eye gaze detection circuitry 24. In other embodiments, the feature detection circuitry 23 and eye gaze detection circuitry 24 may obtain a set of volumetric NCCT data from any suitable data store. The NCCT data may be obtained by the feature detection circuitry 23 and eye gaze detection circuitry 24 at any suitable time after the NCCT scan has been performed.

At stage 32, the feature detection circuitry 23 performs a dense vessel detection procedure. The dense vessel detection procedure comprises processing the volumetric NCCT data received at stage 30 to identify whether a hyperdense artery sign (HAS) is present in the NCCT scan. The hyperdense artery sign may also be referred to as a dense vessel sign.

In the embodiment of FIG. 2, the dense vessel detection procedure is performed using a convolutional neural network, for example using a method as described in Lisowska A., Beveridge E., Muir K. and Poole I. Thrombus Detection in CT Brain Scans using a Convolutional Neural Network. DOI: 10.5220/0006114600240033 In *Proceedings of the 10th International Joint Conference on Biomedical Engineering Systems and Technologies* (BIOSTEC 2017), pages 24-33.

In other embodiments, any suitable method of dense vessel detection may be used. For example, any suitable image analysis techniques may be used to automatically detect dense vessel. A relevant portion of the patient's anatomy may be displayed to the user.

In other embodiments, the feature detection circuitry 23 may be configured to detect any one or more non-contrast imaging features that are associated with occlusion. For example, in some embodiments, magnetic resonance (MRI) data is obtained at stage 30 instead of CT data. The MRI data may comprise a T2* gradient recalled echo (GRE) magnetic resonance study. In such embodiments, the dense vessel detection procedure may comprise processing the MRI data to identify whether a susceptibility vessel sign (SVS) is present in the MRI data.

It is known that the presence in non-contrast studies of certain imaging, such as hyperdense artery sign and susceptibility vessel sign, indicates that an occlusion is present with high specificity but low sensitivity.

In the present embodiment, the feature detection circuitry 23 determines that a region of dense vessel is present if a HAS sign is detected in the NCCT data. The feature detection circuitry 23 may estimate a location of the region of dense vessel.

At stage 34, in response to detection of a region of dense vessel, the notification circuitry 25 designates the patient as a potential thrombectomy candidate. Designating the patient as a potential thrombectomy candidate may also be described as flagging the patient as a potential LVO patient or flagging the patient as a potential thrombectomy patient. The notification circuitry 25 may add the patient to a worklist. The notification circuitry 25 may issue a mobile notification of LVO candidate as described further below with reference to FIG. 3.

The rendering circuitry 26 renders from the NCCT data a rendered image 36 showing a slice aligned to the anterior circulation. The rendered image 36 is aligned to the slice of the NCCT data that is most likely to contain occlusion imaging features.

The display circuitry 28 displays the rendered slice 36 on display screen 16, or on any suitable display. In some embodiments, the detected region of dense vessel is highlighted on the rendered image 36. For example, the detected region of dense vessel may be shown in a different color from the rest of the rendered image 36, or the detected region of dense vessel may be outlined in the rendered image 36.

The rendered image 36 is available for review by a clinician as described below with reference to stage 60.

If no region of dense vessel is detected by the feature detection circuitry 23 at stage 32, stage 34 and/or stage 36 may be omitted in some embodiments. In other embodiments, a slice aligned to the anterior circulation is rendered and displayed even if no dense vessel is detected. In some embodiments, an indication that no dense vessel has been detected may be displayed to the user.

At stage 38, the eye gaze detection circuitry 24 performs an eye gaze detection procedure. The eye gaze detection procedure comprises processing the NCCT scan data to obtain an estimate of a direction of gaze of at least one eye of the patient. In the present embodiment, eye gaze detection is always performed, regardless of the outcome of the dense vessel detection procedure. In some other embodiments, the eye gaze detection may be omitted in some circumstances, for example if dense vessel has already been detected. The eye gaze detection may be performed after the dense vessel detection procedure of stage 32, before the dense vessel detection procedure, or simultaneously with the dense vessel detection procedure.

References to eyes below refer to the globes, which may also be called the eyeballs. If two eyes are present, it is expected that both eyes are looking in the same direction.

An output of the eye gaze detection procedure comprises a classification of the eye gaze direction in the NCCT data into one of three classes. In a first class, the direction of gaze is to the right. In a second class, the direction of the gaze is to the left. In a third class, either the direction of gaze is to neither left or right, or the direction of gaze is unknown. The classifications are referred to below as Right, Left, and Neither/Unknown.

In clinical practice, clinical gaze deviation of the eyes is well documented as a symptom of stroke. Clinical deviation of the eyes is called Prevost's sign. Gaze deviation is defined as equal sustained deviation of both globes from a midline position towards the same side. If present, the eyes deviate to the side of the hemisphere of the brain that has been damaged by stroke. The damaged hemisphere is opposite to the side of the body in which symptoms present, for example paralysis or facial drooping.

An angle of gaze of the eyes may be defined relative to the contralateral plane of the patient's skull. An angle of gaze may be defined as described in, for example, Kobayashi, M., Horizontal gaze deviation on computed tomography: the visual criterion and lesion characteristics in ischemic stroke. Acta Neurol Belg (2018) 118: 581. https://doi.org/10.1007/s13760-018-0949-1 or Spokoyny, Ilana et al., Visual Determination of Conjugate Eye Deviation on Computed Tomography Scan Predicts Diagnosis of Stroke Code Patients, Journal of Stroke and Cerebrovascular Diseases, Volume 25, Issue 12, 2809-2813.

In some embodiments, the eye gaze detection circuitry 24 may return an angle of eye gaze, for example as a numerical value. The angle of eye gaze may be returned in addition to, or instead of, the determination that the direction of eye gaze is Left, Right, or Neither/Unknown.

In the present embodiment, a trained model is used to determine whether the eyes are biased to the right, to the left, or neither/unknown. The trained model may be a deep learning classifier. For example, an R-CNN (regions with convolutional neural network features) method may be used, which may be similar to that described in R. Girshick, J. Donahue, T. Darrell, J. Malik, "Rich feature hierarchies for accurate object detection and semantic segmentation", The IEEE Conference on Computer Vision and Pattern Recognition (CVPR), June 2014. In other embodiments, any suitable method may be used to determine whether the direction of eye gaze is Left, Right, or Neither/Unknown. For example, any suitable image analysis techniques may be used to perform any appropriate classification of direction of eye gaze. A relevant portion of the patient's anatomy may be identified and displayed to the user.

In some circumstances, the scan of the brain may have be obtained such as to exclude the patient's eyes from the anatomical region scanned using the CT scanner. In at least some such cases, it may be possible to obtain a direction of eye gaze based on anatomy other than the globes. For example, a compression of the extraocular muscles may be indicative of an eye gaze direction.

An output of stage 38 is a determination that the direction of eye gaze is Left, Right, or Neither/Unknown.

At stage 40 of FIG. 2, the CT scanner 14 acquires a contrast CT scan (CTA scan) of the brain of the patient.

Volumetric data from the CTA scan is passed to the data store 20, and from the data store 20 to the eye gaze detection circuitry 24. In other embodiments, the eye gaze detection circuitry 24 may obtain a set of volumetric CTA data from any suitable data store. The CTA data may be obtained by the eye gaze detection circuitry 24 at any suitable time after the CTA scan has been performed.

At stage 42, the eye gaze detection circuitry 24 performs an eye gaze detection procedure on the CTA scan data. The eye gaze detection procedure comprises processing the CTA scan data to obtain an estimate of a direction of gaze of at least one eye of the patient. The eye gaze detection circuitry 24 outputs a classification of the eye gaze direction as Right, Left, or Neither/Unknown.

In other embodiments, the eye gaze detection circuitry 24 may return an angle of eye gaze, for example as a numerical value. The angle of eye gaze may be returned in addition to, or instead of, the determination that the direction of eye gaze is Left, Right, or Neither/Unknown.

In the present embodiment, a trained model is used to determine whether the eyes are biased to the right, to the left, or neither/unknown. In some embodiments, the trained model may be different to the trained model used at stage 38, to take account of the determination being performed on contrast data instead of non-contrast data. In other embodiments, the same trained model may be used in stage 38 and stage 42.

An output of stage 42 is a determination that the direction of eye gaze in the CTA data is Left, Right, or Neither/Unknown.

At stage 44, the eye gaze detection circuitry 24 compares the direction of eye gaze determined at stage 38 and the direction of eye gaze determined at stage 42. If the direction of eye gaze determined at stage 42 is the same as the direction of eye gaze determined at stage 38, the eye gaze detection circuitry 24 determines that a sustained deviation in eye gaze direction has occurred. In response to the determining that a sustained deviation in eye gaze direction has occurred, the method of FIG. 2 proceeds to stage 46 and stage 50. If it is determined that no sustained deviation in eye gaze direction has occurred, stage 50 may be omitted. In some embodiments, part or all of stage 46 may also be omitted.

At stage 46, the notification circuitry 25 designates the patient as a potential thrombectomy candidate in dependence on the direction of eye gaze being the same in the CTA data and the NCCT data. If the patient has already been designated as a potential thrombectomy candidate at stage 34, no change is made to the designation of the patient as a potential thrombectomy candidate.

It has been shown that sustained eye deviation across NCCT and CTA has good sensitivity and specificity for large vessel occlusions (Attenhofer et al, The Sustained Deye-COM Sign As a Predictor of Large Vessel Occlusions and Stroke Mimics, J. Stroke Cerebrovasc Dis. 2018 June; 27(6); 1466-1470). Sustained eye deviation is used in the method of FIG. 2 as one indicator that the patient is a potential thrombectomy candidate.

The rendering circuitry 26 receives from the eye gaze detection circuitry 24 an indication of an eye region within the volumetric NCCT data and/or within the CTA data. For example, the eye region may be indicated by a bounding box obtained from segmentation. The rendering circuitry 26 renders from the volumetric NCCT data and/or CTA data at least one image 48 showing the eye region. In the present embodiment, the rendered image 48 is representative of a portion of an axial slice through the head which passes through the lenses of the eyes.

The display circuitry 28 displays the at least one rendered image 48 of the eye region on the display screen 16. The at least one rendered image 48 may provide a quick view of eye gaze. The at least one rendered image 48 may provide a snapshot of the eyes, which is included to indicate a side of the suspected occlusion.

By displaying the snapshot of the eyes, a clinician may be directed to a hemisphere of the brain that corresponds to the eye gaze direction. The clinician may use the indication of side of the brain to identify an occlusion.

In other embodiments, derived measurements related to eye gaze deviation may also be displayed. For example, an angle of deviation may be displayed. In further embodiments, any other clinical information may be displayed.

Various methods of displaying a view of eye gaze are described further below with reference to FIGS. 8a to 10c. Derived measurements or other clinical information may also be displayed along with any of the views of eye gaze described below.

At stage 50, the rendering circuitry 26 renders a set of CTA views 52, 54, 56, 58. The display circuitry 28 displays the CTA views 52, 54, 56, 58 on display screen 16 in accordance with a set of display rules, for example a hanging protocol. The display of the CTA views may be optimized to allow human recognition of an occlusion.

The CTA views 52, 54, 56, 58 are stroke views which are based on landmarks in the CTA. Stroke views may be views that review specific anatomical and vascular regions of the brain that are relevant to stroke. A first view 56 is the anterior circulation, the second and third views 54, 58 are two views of the posterior circulation and the fourth view 52 is a view of the collateral circulation. The CT views 52, 54, 56, 58 are displayed according to selected display parameters. The images of the CTA views 52, 54, 56, 58 are aligned to anatomy. The images are slabbed to a selected thickness with window levels set to selected values. The selected values for thickness and window levels may considered to be optimum values for the anatomy that is being viewed and/or for the pathology that is being viewed.

In this embodiment, the CTA views 52, 54, 56, 58 are only displayed if sustained eye deviation is detected. If sustained eye deviation is detected, a first display mode is used in which the CTA views 52, 54, 56, 58 are displayed. If no sustained eye deviation is detected, a second display mode is used in which the CTA views 52, 54, 56, 58 are not displayed. The display circuitry 28 is configured to display the most appropriate scan for a given result or criteria.

In other embodiments, for example as described below with reference to FIGS. 6 and 7, the display circuitry 28 displays both the rendered image 36 of a slice aligned to the anterior circulation and the CTA views 52, 54, 56, 58, but the type of display differs in dependence on the determined eye gaze deviation. If sustained eye gaze deviation has been detected, a first display mode is used in which the CTA views 52, 54, 56, 58 are provided as a large, primary image display and the rendered image 36 comprising a slice aligned to anterior circulation is provided as a smaller image, for example a thumbnail image. If no sustained eye gaze deviation has been detected, a second display mode is used in which the rendered image 36 comprising a slice aligned to anterior circulation is provided as a large, primary image display and the CTA views 52, 54, 56, 58 are provided as smaller images, for example thumbnail images. The clinician may select smaller images to view those images in full detail, for example by clicking on the smaller images.

A display mode may be based on times at which the scans were acquired, or on an interval between the times at which the scans were acquired, for example by using an elapsed time between scans.

At stage 60, a clinician reviews the rendered image 36 comprising a slice aligned to anterior circulation if dense vessel sign has been detected at stage 32. The clinician reviews the CTA views 52, 54, 56, 58 if sustained eye deviation has been detected at stage 44. The display of images 36, 52, 54, 56, 58 may be such that the clinician is presented with the most relevant images for initial review. The clinician considers the patient for thrombectomy. The clinician may identify the patient as suitable for thrombectomy. The clinician may choose to transfer the patient.

Pre-configured criteria for thrombectomy and/or transfer may be used. A panel 62 of thrombectomy and/or transfer criteria may be displayed to the clinician. Thrombectomy and/or transfer criteria and their display on a panel 62 is described below with reference to FIGS. 4 to 7.

Figure 3:
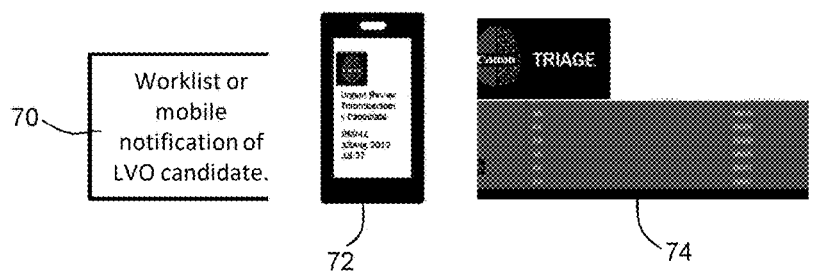
FIG. 3 is a schematic illustration of a notification in accordance with an embodiment.

FIG. 3 illustrates a notification procedure 70 which may be performed as part of stage 36 or stage 46 of FIG. 2. In the present embodiment, the notification procedure 70 comprises a worklist or mobile notification of an LVO candidate.

The mobile notification comprises a message that is sent to a mobile device, for example a smartphone 72. The message indicates that an urgent review of a potential thrombectomy candidate is required.

The workflow notification comprises an indicator that is placed on a workflow 74. The workflow comprises a list of patients for whom data is to be reviewed. An indicator is added to one of the patients to suggest that an urgent review of that patient is performed. In some embodiments, the workflow may be reordered so that the patient that has been identified for urgent review is moved up the list of patients.

The mobile notification or workflow notification may comprise summary information about the patient's condition.

On receiving a notification, for example a mobile notification or workflow notification, a clinician may decide to prioritize review of the patient for whom the notification has been issued. A time before a patient is reviewed a patient may be reduced. A time between scan acquisition and treatment, for example thrombectomy, may be reduced.

The method of FIG. 2 and FIG. 3 may provide a method of presenting clinically relevant information to determine the presence of large vessel occlusions and to identify thrombectomy candidates in acute stroke patients. Sustained eye gaze detection is performed across successive images. In the method of FIG. 2, the successive images comprise NCCT data and CTA data respectively. The method of FIG. 2 also identifies non-contrast imaging features which are associated with occlusion. Cases are flagged based on sustained eye deviation or presence of an occlusion imaging feature, which in the present embodiment is a dense vessel sign. A clinician is notified if the patient is found to meet the criteria for a potential thrombectomy candidate.

A display mode may be selected in such a way as to expedite review of a potential thrombectomy candidate. The clinician may be presented with the most relevant information first. The clinician may use the most relevant information in assessing whether an occlusion is present.

Relevant information is provided to the clinician without the image processing apparatus 10 performing any direct detection of LVO.

In some embodiments, additional pre-defined inclusion or exclusion criteria may be incorporated into the method described above with reference to FIGS. 2 and 3. For example, ASPECTS or ICH may be used. Such embodiments are described below with reference to FIGS. 4 to 7.

Figure 4:
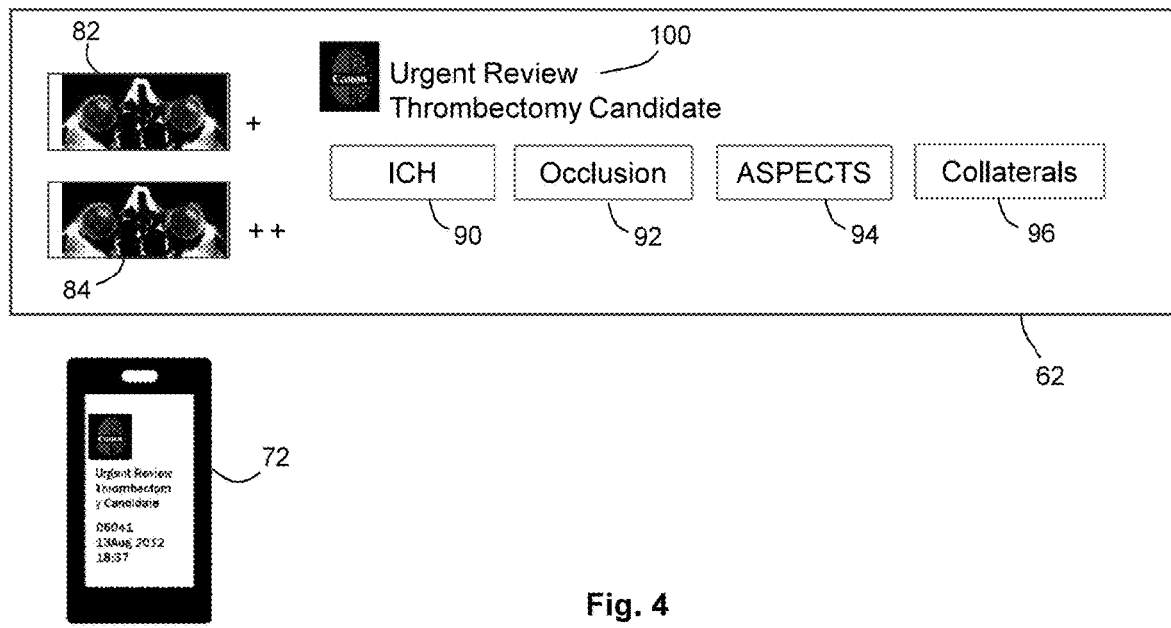
FIG. 4 is a schematic illustration of a user interface in accordance with an embodiment.

FIG. 4 illustrates elements of a user interface on which information is displayed to a user, for example a clinician. The user interface may be displayed on any appropriate screen, for example display screen 16. FIG. 4 also illustrates a smartphone 72 on which a notification message is displayed.

The user interface comprises a panel 62. Two views 82, 84 of an eye region of a patient are displayed on panel 62. A first view 82 is obtained by rendering image data from a first scan that is obtained at a first time point. In the embodiment illustrated in FIG. 4, the first scan is an NCCT scan. The patient's eyes are deviated to the left in the first scan. A plus sign (+) is displayed beside the first view 82 to indicate the eyes are deviated in the first view 82. A plus sign would also be displayed if the eyes were deviated to the right. A minus sign (−) would be displayed if no eye deviation were present.

In other embodiments, any suitable indicator or indicators of eye deviation may be used. Any suitable visual effects may be used to highlight or emphasize eye deviation, for example visual effects as described below with reference to FIGS. 8*a* to 10*c*.

A second view 84 is obtained by rendering image data from a second scan that is obtained at a second time point. In the embodiment illustrated in FIG. 4, the first scan is a CTA scan. The patient's eyes are deviated in the second scan in the same way as in the first scan. Two plus signs are displayed beside the second view 84 to indicate that the patient's eyes are consistently deviated in both scans. In other embodiments, any suitable indicator or indicators may be used to indicate sustained deviation. Any suitable visual effects may be used to highlight the sustained deviation.

The first and second views 82, 84 are axial slices that are each aligned with the eye lenses of the patient to indicate an affected side for each scan. The first and second views 82, 84 provide a snapshot of the eyes for two successive scans at two successive time points, which are rendered as two successive images. It is known that if an eye deviation is sustained across both images, it is likely that the patient may have LVO. The first and second views 82, 84 may be from any two successive scans and images. In the embodiment of FIG. 4, the two successive scans are NCCT and CTA.

In other embodiments, one or both of the scans may be an MRI scan. In some embodiments, the scans comprise two MRI sequences in which the eyes are visible. SVS for dense vessel is substituted by GRE.

In other embodiments, the scans may be a 3D scanogram obtained at a first time point and an NCCT scan obtained at a second time point. When performing a CT scan of a region of a patient's body, it is common to first perform a three-dimensional (3D) scanogram. The 3D scanogram may have a larger field of view that the local scan of the region that is to be performed. The 3D scanogram may comprise a low-resolution scan of a larger region of the patient's body, for example the whole of the patient's body. The use of an NCCT 3D scanogram followed by an NCCT scan may provide an NCCT-only solution for referring centers.

In some embodiments, the first scan is an optical image obtained by an optical camera in the scanner. Eye deviation is determined in the optical image and in a subsequent scan. In some embodiments, a video camera, for example an AI video camera, is used for imaging to determine eye deviation, and the eye deviation in video obtained by the video camera is compared with eye deviation in a subsequent scan.

Having the first and second views 82, 84 of the eye region always present may indicate a side of an abnormality to the user. A side of an abnormality may be indicated to the user without outputting results to the user, for example without outputting an explicit indication that the patient may have LVO. In some circumstances, requirements for regulatory approval may be different for systems that display a diagnosis than for systems that do not provide a diagnosis. Providing relevant information to a user without providing a diagnosis may be important for regulatory clearance. A tool may avoid CADe (Computer Aided Detection) and thus be less difficult for regulatory approval.

In FIG. 4, the panel 62 also includes information about criteria for factors other than eye deviation. In the embodiment of FIG. 4, the criteria relate to ICH (intracerebral hemorrhage), occlusion, ASPECTS (Alberta stroke program early CT) score, and collaterals. A first display element 90 represents ICH (intracerebral hemorrhage) score. A second display element 92 represents occlusion information. A third display element 94 represents ASPECTS (Alberta stroke program early CT) score. A fourth display element 96 represents collaterals. Together, the first to fourth display elements 90, 92, 94, 96 and views 82, 84 may be considered to provide a set of clinically relevant information to determine the presence of LVOs and thrombectomy candidates in acute stroke patients.

To provide a full LVO triage solution, other criteria (for ICH, occlusion, ASPECTS, collaterals) are considered in combination with the eye gaze deviation shown in the first and second views 82, 84. In some embodiments, a hospital may configure a display by selecting which information relating to criteria to display. The selection of which information relating to criteria to display may be based on the imaging available, for example the imaging available in that hospital or the imaging available for an individual patient.

In the embodiment of FIG. 4, each of the display elements 90, 92, 94, 96 is flagged as green when results associated with that display element 90, 92, 94, 96 meet thrombectomy or transfer criteria. For example, display element 90 is colored green when the ICH score meets predefined thrombectomy or transfer criteria. The green color is not represented in FIG. 4 because FIG. 4 is in black and white.

In other embodiments, any suitable method may be used to indicate that results for a display element 90, 92, 94, 96 meet thrombectomy or transfer criteria. For example, any suitable color, line style, shape or shading or any suitable visual effect or other effect may be used.

If results for all of the factors represented by display elements 90, 92, 94, 96 meet the thrombectomy or transfer criteria, a notification 100 is displayed on the panel 62. In the example of FIG. 4, a text of the notification is 'Urgent Review Thrombectomy Candidate'. By displaying the notification 100, a clinician may be triggered to urgently review the patient's imaging to determine whether the patient is a thrombectomy candidate.

Figure 5:
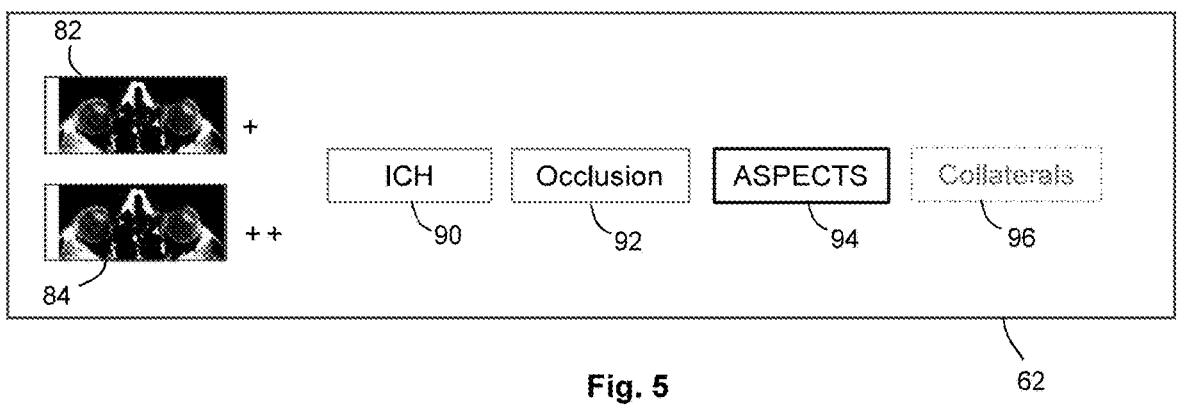
FIG. 5 is a schematic illustration of a user interface in accordance with an embodiment.

FIG. 5 illustrates an example in which results for thrombectomy or transfer criteria are contradictory or missing. Panel 62 comprises first and second views 82, 84 and display elements 90, 92, 94, 96 similar to those of FIG. 4. As in FIG. 4, sustained eye deviation is indicated by a plus sign on first view 82, and by two plus signs on second view 84.

In the example shown in FIG. 5, ICH results and occlusion results both meet criteria for thrombectomy or transfer, and so display elements 90 and 92 are flagged as green (green color not shown in FIG. 5). The green display indicates that inclusion criteria are met. The inclusion criteria are indicative of an occlusion being present within a certain location.

Results obtained from an algorithm to determine an ASPECTS score are a contraindication to thrombectomy or transfer criteria. Display element 94 is flagged as red (the red color not shown in FIG. 5, but is instead represented by a bold outline).

In the embodiment of FIG. 5, any of display elements 90, 92, 94, 96 may be flagged in red if their results are a contraindication to thrombectomy or transfer.

A contraindication may occur even if other criteria are met. For example, an occlusion may be present, but the patient may be excluded for treatment based on another imaging feature, such as poor collaterals, or some other clinical information.

In other embodiments, any suitable method may be used to indicate that a results for a display element 90, 92, 94, 96 are a contraindication to thrombectomy or transfer criteria. For example, any suitable color, line style, shape or shading or any suitable visual effect or other effect may be used.

In the embodiment shown in FIG. 5, no appropriate scan or results are available to provide information on collaterals. Display element 96 is greyed out to indicate that results are not available. In other embodiments, any of display elements 90, 92, 94, 96 may be greyed out if no appropriate results are available for a factor associated with that display element. In other embodiments, any suitable method may be used to indicate that a results for a factor associated with a display element 90, 92, 94, 96 are a not available. In some embodiments, the display element may be hidden entirely. In other embodiments, any suitable color, line style, shape or shading or any suitable visual effect or other effect may be used.

Having a list of criteria to be reviewed (in this embodiment, ICH, occlusion, ASPECTS and collaterals) may serve as a checklist for a clinician to check for all relevant pieces of information. The clinician may check for the relevant pieces of information whether or not automated results for the criteria are provided.

Figure 6:
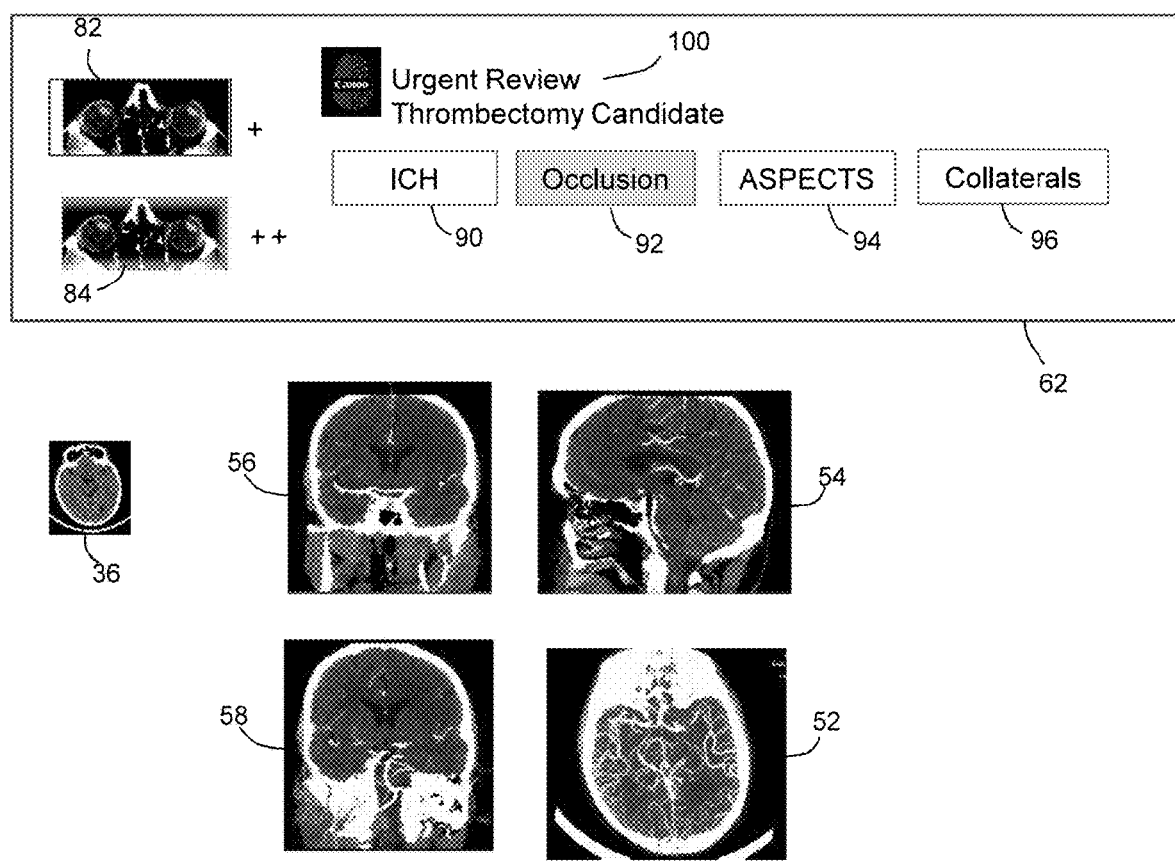
FIG. 6 is a schematic illustration of a user interface in accordance with an embodiment in which sustained eye deviation is present.

FIG. 6 is representative of an interaction of a clinician with the panel 62. Panel 62 displays first and second views 82, 84 of the patient's eye region and display elements 90, 92, 94, 96 representing ICH score, occlusion, ASPECTS score and collaterals respectively. First and second views 82, 84 both show deviation of eye gaze, which is additionally indicated by a plus sign on first view 82 and two plus signs on second view 84. All factors associated with the display elements 90, 92, 94, 96 meet thrombectomy or transfer criteria and are highlighted in green (not shown in FIG. 6).

The clinician reviews the factors represented by the display elements 90, 92, 94, 96 (ICH, occlusion, ASPECTS, collaterals) against the thrombectomy or transfer criteria. When the clinician selects each of the display elements 90, 92, 94, 96, for example by clicking on the display element, relevant information is displayed to the clinician. For example, appropriate imaging may be displayed.

FIG. 6 shows an example in which the clinician has selected occlusion, for example by clicking on display element 92. Fill shading on display element 92 is used to indicate that display element 92 has been selected. In other embodiments, any suitable visual indication may be used to indicate that one of the display elements 90, 92, 94, 96 has been selected.

On selection of one of the criteria (ICH, occlusion, ASPECTS, collaterals) by the clinician, the display circuitry 28 selects the most appropriate scan to view for that criteria. In the example shown in FIG. 6, the patient has sustained eye deviation but no dense vessel. When the clinician selects occlusion by selecting display element 92, the display circuitry 28 displays a set of stroke views 52, 54, 56, 58 for quick review of key LVO locations in vasculature.

The display circuitry also highlights the view of the eyes that corresponds to the scan being viewed. The scan that is being shown is highlighted so that eye and side information is always highlighted.

In FIG. 6, the stroke views are obtained from the second (CTA) scan, so the second view 84 of the eyes is highlighted. In the example of FIG. 6, the second view 84 is highlighted using a halo effect around the second view 84. In other embodiments, any suitable visual effect or other effect may be used to highlight the scan being viewed.

In addition to the stroke views 52, 54, 56, 58 that are being presented to the clinician, all other scans remain available to view as normal. For example, the slice 36 aligned to the anterior circulation is displayed in FIG. 6 as a small thumbnail image which is available for selection by the clinician.

Once the clinician starts to review criteria, if they select a display element associated with any criterion or criteria, the display circuitry 28 selects the most appropriate scan to view for that criterion or criteria. For example, if ICH is selected, the display circuitry 28 automatically shows the NCCT, or the GRE in embodiments in which an MRI scan is obtained. The most appropriate scan to show may depend on the workflow and imaging used. A choice of the most appropriate scan to show may be configured by a hospital.

Figure 7:
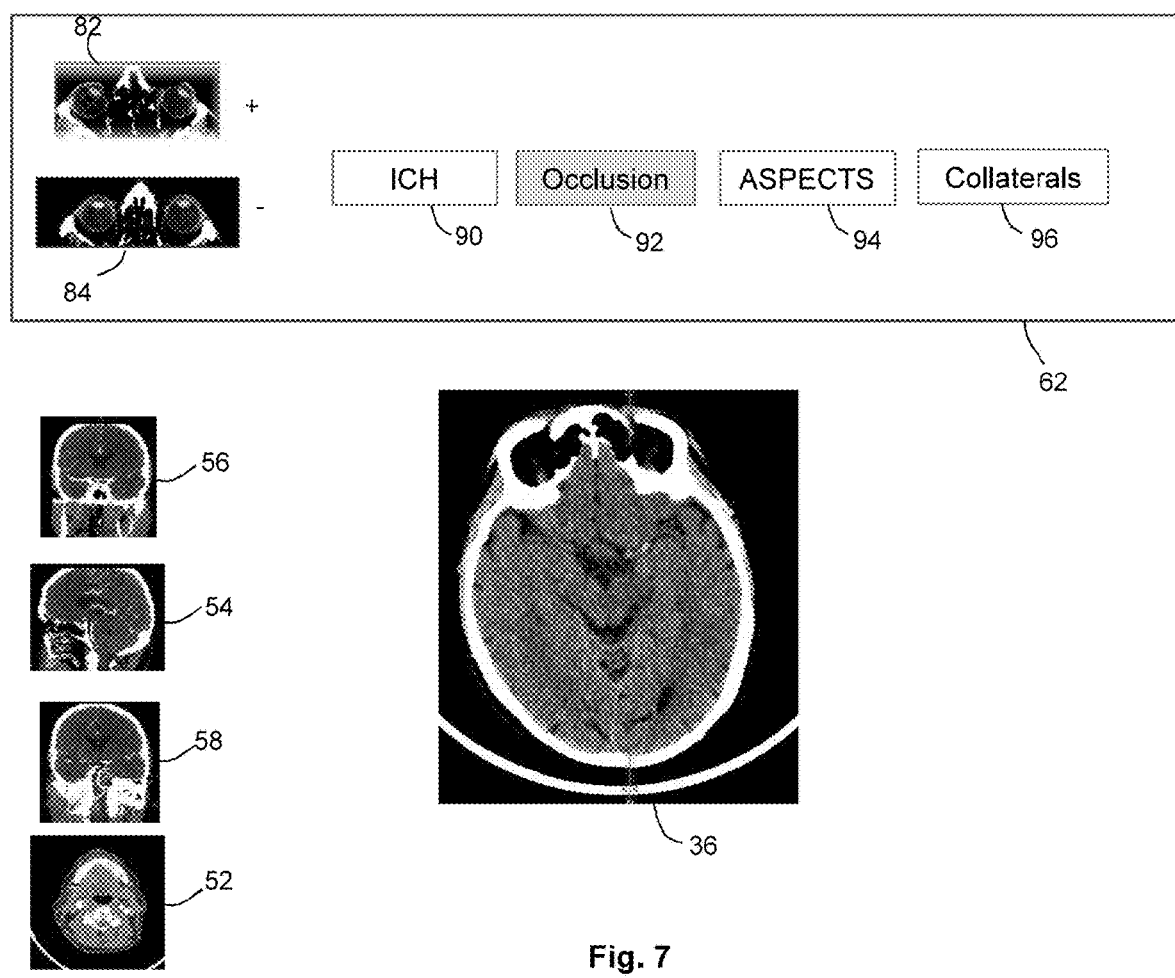
FIG. 7 is a schematic illustration of a user interface in accordance with an embodiment in which dense vessel is present.

FIG. 7 shows selection of occlusion by the clinician from panel 62 in a case in which the patient did not display sustained eye deviation, but had dense vessel sign. Panel 62 displays first and second views 82, 84 of the patient's eyes and display elements 90, 92, 94, 96 representing thrombectomy or transfer criteria. All criteria of display elements 90, 92, 94, 96 meet thrombectomy or transfer criteria and are highlighted in green (not shown in FIG. 7).

In the first view 82 of the patient's eyes, deviation is present, which is represented by a plus sign beside the first view 82. In the second view 84 of the patient's eyes, no deviation is present. A minus sign is included beside the second view 84. The eye gaze detection circuitry 24 determines that there is no sustained eye gaze deviation.

When the clinician selects the display element 92 representing occlusion, the display circuitry 28 selects the most appropriate scan. Since the patient does not have sustained eye deviation, but has dense vessel sign, the scan that is selected as the most appropriate scan to show first is the NCCT. The first view 82 is highlighted to show that the NCCT scan is being viewed. In FIG. 7, the first view 82 is highlighted by a halo effect around first view 82.

The NCCT scan is shown in this embodiment by displaying the a pre-set slice output 36 which is aligned to the most likely slice of the anterior circulation. The slice 36 is selected as the most likely slice in which to see dense vessel. Selection of the most likely slice 36 by the rendering circuitry 26 may reduce an amount of scrolling through images required, such that minimal scrolling is required.

In some embodiments, the display of the slice 36 may include segmentation of dense vessels. In some embodiments, the display of the slice 36 may include labelling of dense vessels. The presence of segmentation and/or labelling may in some circumstances depend on a regulatory approach.

In the embodiment of FIG. 7, stroke view pre-sets 52, 54, 56, 58 are still available after viewing of dense vessel. The clinician may view one or more of the stroke views 52, 54, 56, 58 by selecting them from thumbnail views, or in any suitable manner. The most appropriate stroke view pre-sets may be selected based on the location of the dense vessel. In some embodiments, the display circuitry 28 automatically selects the most appropriate stroke view pre-sets based on predetermined rules. In some embodiments, the stroke view pre-sets may be determined by the clinician.

In the embodiments illustrated in FIGS. 6 and 7, the display circuitry 28 selects the most appropriate scan and view for chosen criteria. When occlusion is selected and dense vessel is present without sustained eye gaze deviation, the display circuitry 28 uses an alignment to slices that are most likely to contain circulation in non-contrast scan for a quick review of occlusion related imaging features. When occlusion is selected and sustained eye gaze deviation is present, the display circuitry 28 displays a presentation of stroke views in CTA for quick review of vasculature. If neither dense vessel nor sustained eye deviation is detected, a default view of the NCCT scan is displayed. The default view of the NCCT scan may be a default display of the NCCT scan upon loading into a viewer. In other embodiments, any suitable view or views may be displayed.

Different scans may be displayed for different criteria. Different scans may be displayed for different results. The display circuitry 28 also selects the most appropriate view for each scan (for example, stroke views).

The panel 62 provides an interaction display of information that is relevant to thrombectomy or transfer criteria. In some embodiments, a summary view may be provided as an addition or an alternative to the panel 62. A presentation of information may be determined and presented to a user in summary form. For example, the information may be displayed as a report or as another non-interactive view format.

FIGS. 8a to 8c and 9a to 10c represent methods of displaying eye gaze on a user interface to highlight sustained deviation across scans. The highlighting of sustained deviation may allow a quick determination of the sustained deviation by the user, for example a clinician, and therefore may allow for a quick assessment of whether a patient is a candidate for thrombectomy or transfer. Eye display in accordance with FIG. 8a to 8c or 9a to 10c may be substituted for the views 82, 84 shown in FIGS. 4 to 7.

Figure 8A:
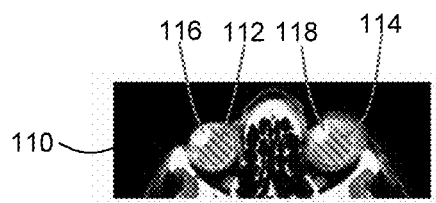
FIGS. 8a to 8c are views of a patient's eyes in which eye gaze direction is highlighted in accordance with an embodiment.
Figure 8B:
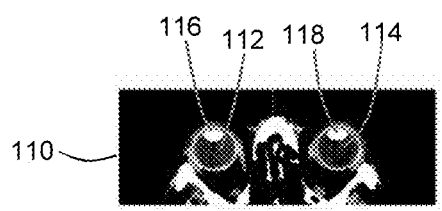
Figure 8C:

FIGS. 8a to 8c represent a user interface in an embodiment in which a hatch is used to highlight directions of deviation.

In each of FIGS. 8a to 8c, the eye gaze detection circuitry 24 has segmented the globe 112, 114 and lens 116, 118 of each eye. Any suitable segmentation method may be used. The rendering circuitry 26 renders an image in which each segmented globe 112, 114 is outlined. Each segmented lens 116, 118 is represented by a respective graphic element, which in the images of FIGS. 8a to 8c is a filled element in solid white.

Eye deviation is shown by hatching of the segmented globes. In FIG. 8a, eye deviation to the patient's right is shown by hatching comprising diagonal lines which are aligned with a direction of gaze. In FIG. 8b, there is no deviation and therefore no hatching is used. In FIG. 8c, eye deviation to the patient's left is shown by diagonal hatching which is aligned with a direction of gaze.

In other embodiments, any suitable graphic elements may be used to emphasize the globe and/or the lens. Any suitable pattern or visual feature may be used to highlight the direction of eye gaze. For example, an arrow may be used to indicate the direction of eye gaze.

in some embodiments, different colors are used to represent different scans, such that a color in which the eyes are rendered changes for different scans across different time points. A first color may be used in rendering the eyes in an image derived from a scan at time point 1. A second color may be used in rendering the eyes in an image derived from a scan at time point 2. A first color may be used in rendering the eyes in an image derived from a scan at time point 3. The use of color may be combined with the use of other visual effects, for example hatching.

FIGS. 9a to 10c represent a user interface in an embodiment in which both hatching and color are used to highlight directions of deviation. Color is not shown in FIGS. 9a to 10c, which are in black and white.

A single image 120 is used to represent the eye region of the patient. Two or more scans (for example, NCCT and CTA scans) obtained at respective time points are registered together such that they can be displayed on the same image.

Figure 9A:
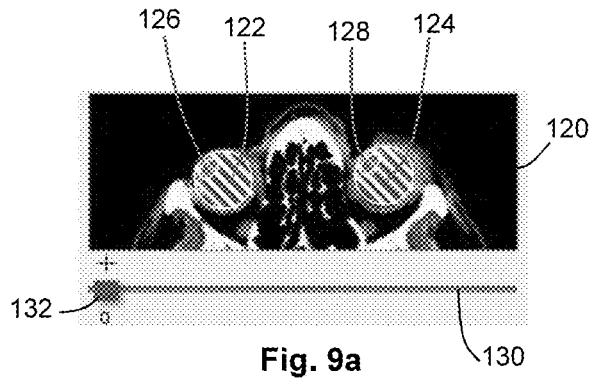
FIGS. 9a to 9c are views of a patient's eyes in which eye gaze direction is highlighted in accordance with an embodiment.
Figure 9B:
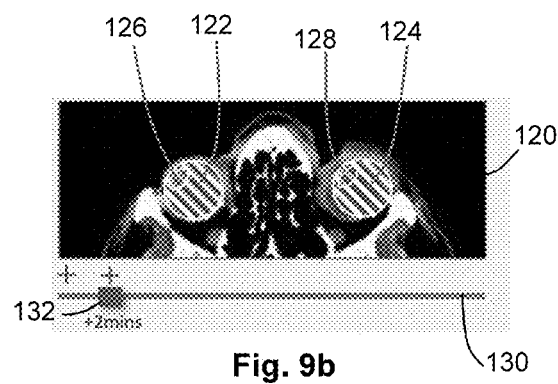
Figure 9C:
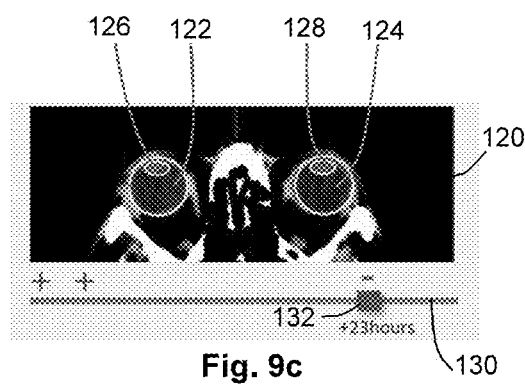

A slider bar 130 represents time and is used to switch between views of the two or more scans. A user moves an indicator 132 of the slider bar 130 to change between views that are representative of different times. In the embodiment of FIGS. 9a to 9c, a scale of the slider bar 130 represents an elapsed time since the first scan, which is shown as time=0. In other embodiments, a scale of the slider bar 130 may show actual times of the scans.

FIGS. 9a and 9b represent an example in which sustained deviation is present (DeyeCOM+/+). In FIG. 9a, a baseline scan is shown. The baseline scan is representative of eye deviation at time=0, as shown on the slider bar 130. An eye detection and lens segmentation is performed and used in highlighting the eyes of the patient in the baseline scan. In the embodiments of FIGS. 9a to 9c, each globe 122, 124 is outlined and each lens 126, 128 is outlined. In other embodiments, any suitable method of highlighting the globes and/or lenses may be used.

In FIG. 9a, a direction of eye deviation in the baseline scan is shown by red and white hatching aligned with the eye gaze direction (red color not visible in FIG. 9a). A red plus sign is displayed at time=0 on the slider bar 130. An indicator 132 of the slider bar is positioned at time=0.

In FIG. 9b, the indicator 132 is moved to a position of time=+2 minutes and the image 120 shows a second scan obtained 2 minutes after the baseline scan. An eye detection and segmentation in the second scan are registered to the baseline scan. In the second scan, a direction of eye deviation in the second scan is shown by green and white hatching aligned with the eye gaze direction (green color not visible in FIG. 9b). A green plus sign is also displayed at time=+2 minutes on the slider bar 130. The globes 122, 124 and lenses 126, 128 are outlined.

In the embodiment of FIGS. 9a and 9b, moving the indicator 132 of the slider bar 130 between time points at 0 and at +2 minutes causes the color of the image 130 to fade between the red at 0 and green at +2 minutes. The image shown may fade between the image shown at 0 and the image shown at +2 minutes.

A user can see at a glance if the deviation is sustained. The user can move the indicator 132 back and forward on the slider bar 130 to switch between the baseline scan and the second scan. The use of color may allow the user to distinguish easily between the baseline scan and second scan. Colors may be faded gradually between time points. The slider bar 130 and changing color may provide an intuitive way of showing the eye gaze deviation in the baseline scan and second scan.

In other embodiments, no fading between images is present. In some embodiments, images at 0 and at +2 minutes may be overlaid. In further embodiments, any suitable visual method may be used to combine or transition between the image at 0 and the image at +2 minutes.

In some circumstances, a baseline scan and second scan may be followed by a follow-up scan that is taken at a longer interval after the second scan. The follow-up scan may not be acute but may be used to see whether an acute condition is resolved.

FIG. 9c shows an example of a follow-up scan. The follow-up scan is registered with the baseline scan. Results of the follow-up scan are shown on image 120 when a user slides the indicator 132 of the slider bar 130 to the time of the follow-up scan. In FIG. 9c the time of the follow-up scan is +23 hours, which is 23 hours after the baseline scan. The slider 130 is not provided as a linear scale. Instead, a scale of the slider bar 130 is selected so that the scan times of 0, +2 minutes and +23 hours are all easily distinguishable and fit onto the same scale.

In the follow-up scan of FIG. 9c, no eye deviation is present. The eyes are colored in blue (blue color not shown in FIG. 9c). No hatching is present. A minus sign is displayed along with the time of +23 hours on the slider bar 130. The minus sign is shown in blue (blue color not shown in FIG. 9c).

By sliding the indicator 132 along the slider bar 130, the user may switch between two or more scans and may see eye deviation across multiple time points. The image may fade between the different scans.

Figure 10A:
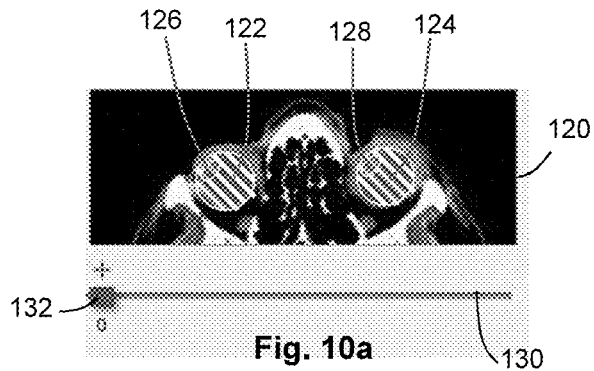
FIGS. 10a to 10c are views of a patient's eyes in which eye gaze direction is highlighted in accordance with an embodiment.
Figure 10B:
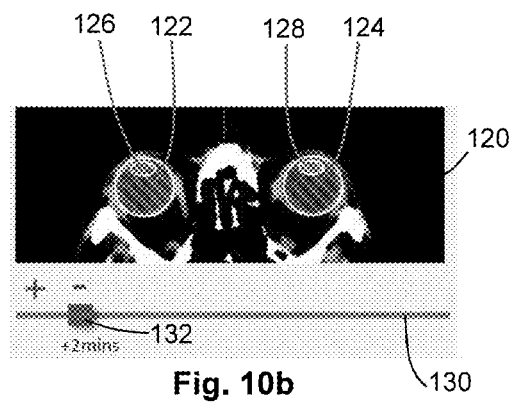

FIGS. 10a and 10b represent the same display as in FIGS. 9a and 9b, but for an example in which no sustained deviation is present (DeyeCOM+/−). FIG. 10a shows image 120 at time=0. FIG. 10a is representative of a baseline scan, for example an NCCT scan, and is the same as FIG. 9a. The indicator 132 of the slider bar 130 is positioned at time=0. Eye deviation is indicated by red and white hatching of the globes 122, 124 (the red color is not shown in FIG. 10a). The hatching is aligned with a direction of eye gaze. Eye deviation is also indicated by a plus sign at time=0.

In FIG. 10b, a second scan at time=+2 minutes, for example a CTA scan, is shown in image 110. The second scan is registered to the baseline scan of FIG. 10a. The indicator 132 of the slider bar 130 is positioned at time=+2 minutes.

In FIG. 10b, there is no eye gaze deviation. The globes are shaded in green, which is representative of the time point (the green color is not shown in FIG. 10b). A greyed-out version of hatching is shown in the globes. The greyed-out hatching indicates to the user that there has been a previous eye gaze deviation that is now no longer present. In other embodiments, any suitable method of visual indication of eye gaze direction or change of eye gaze direction may be used.

A minus sign is shown by the slider bar 130 at time=+2 minutes.

When the user moves the indicator 132 of the slider bar 130 between time=0 and time=+2 minutes, the color fades between the colored scans to see the shift in gaze direction between a red and white hatched image at time=0 and a green and grey hatched image at time=+2 minutes. The user interface allows fading between the colored scans to see the shift in gaze orientation.

Figure 10C:
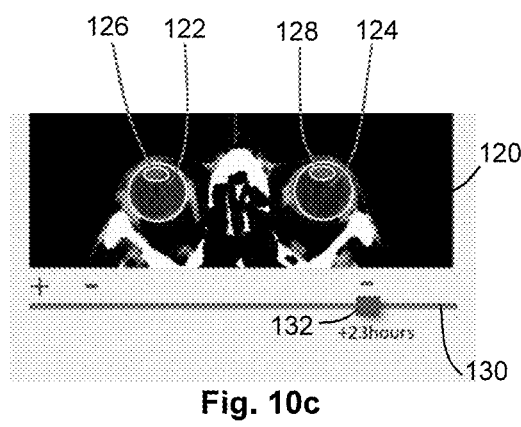

FIG. 10c shows results of a follow-up scan in image 110. The follow-up scan is registered to the baseline scan of FIG. 10a. The follow-up scan is taken at a time of +23 hours. The follow-up scan shows no eye gaze deviation. The globes are shaded in blue (the blue color is not shown in FIG. 3c) and a blue minus sign is shown by the slider bar 130 at time=+23 hours.

In the embodiment of FIGS. 9a to 10c, the data is registered and the eye and the lens are segmented and given a distinct color for each scan. The image 120 fades between images of different scans as the indicator 132 of the slider bar 130 is moved between time points.

Although scans at particular times (0, +2 minutes, +23 hours) are used as examples in FIGS. 9a to 9c, in other embodiments scans may be obtained at any suitable time points. Any suitable time intervals and ranges of time may be displayed.

In some embodiments, a geometry of the eye is morphed across the scans to show movement. For example, a representation of the lens may be moved from a first position in the baseline scan to a second position in the second scan. The representation of the lens may be moved in a continuous manner, such that the eye appears to be rotating between the first position and the second position.

In some embodiments, a sequence between images of two or more scans is automatically cycled between views of the scans when the user performs a triggering action. For example, the triggering action may be hovering over the image 120, or hovering over the slider bar 130. The images of the two or more scans may be automatically cycled back and forth. The automatic cycling may comprise fading between the images. The automatic cycling may comprise morphing between the images. In some embodiments, a video of a fading or morphing sequence may be automatically saved as a capture. The video may be saved in data store 20 or in any other suitable data store. The video may be saved in PACS.

In the embodiment of FIGS. 9a to 10c, the segmented lens and segmented eye are each outlined using solid lines in image 120. In other embodiments, the outline of the lens and/or the outline of the eye may be visualized with a different line style for each scan. For example, the lens and eye in the baseline scan may be outlined using a solid line and the lens and eye in the second scan may be outlined using a dashed line.

Methods similar to that described above with reference to FIGS. 2 and 3 and interfaces similar to those described above with reference to FIGS. 4 to 10c may be used to process and display any suitable data. Any suitable modality or modalities of data may be used, for example CT data, cone-beam CT data, X-ray data, ultrasound data, MR data, PET data or SPECT data. Any appropriate first and second scans may be used.

The scans may be of any suitable patient or other subject. Displayed images and data may be reviewed by any suitable user, for example any appropriate clinician or researcher. In some embodiments, an image or representation of a single eye of the patient may be displayed rather than displaying an image or representation of both eyes.

Certain embodiments provide a medical imaging apparatus comprising
  A method of presenting clinically relevant information flagging potential LVO/thrombectomy patients in which
    At least one part of the information includes (sustained) eye gaze deviation The eye deviation may be automatically detected using image analysis techniques where the relevant portion of anatomy is also identified and displayed to the user.

Dense vessel may be automatically detected using image analysis techniques and the relevant portion of anatomy may also be identified and displayed to the user.

CTA views optimized to allow human recognition of an occlusion may automatically be determined and presented to the user.

Other clinically relevant information may be detected/displayed.

A presentation may be determined and presented to the user in summary form (such as a report, or other non-interactive view format).

The presentation may allow UI.

A notification may be delivered (e.g. smartphone, with layout and summary information).

A worklist is prioritized according to the automatically detected information.

Direct LVO detection or other CADe may also be included in the display.

Derived measurements related to eye gaze deviation or any other clinical information may be displayed.

The data may be registered and the eye and the lens may be segmented and given a distinct color for each scan.

The user interface may allow fading between the colored scans to see the shift in gaze orientation.

The geometry of the eye may be morphed across the scans to show the movement instead of the grayscale shift.

A sequence may be automatically cycled back and forth when the user hovers over the view.

A video of the fading/morphing sequence may be automatically saved as a capture in PACS.

For the report, only an outline of the lens and eye from both scans may be visualized with different line style for each scan (for example solid for one and dashed for the other).

Certain embodiments provide an image displaying apparatus comprising processing circuitry configured to: receive medical image data including at least patient's eye, control a displaying mode of the medical image data based on a deviation angle of the patient's eye.

The processing circuitry may be further configured to: receive a plurality of medical image data which are scanned at least two different time points, control a display mode of the plurality of medical image data based on the time points.

The processing circuitry may be further configured to: receive a plurality of medical image data which are scanned at least two different time points, control a display mode of plurality of the medical image data based on the interval of the time points.

Certain embodiments provide a medical data processing apparatus comprising processing circuitry configured to: receive first medical imaging data representative of a first scan of a subject; automatically process the first medical imaging data to determine a first eye gaze direction of the subject; receive second medical imaging data representative of a second, subsequent scan of the subject; automatically process the second medical imaging data to determine a second eye gaze direction of the subject; use the first eye gaze direction and second gaze direction to determine whether a sustained eye gaze deviation has occurred; identify whether the subject is a potential large vessel occlusion (LVO) or thrombectomy candidate, wherein the identifying is in dependence on whether a sustained eye deviation has occurred; and if the subject is identified as a potential LVO or thrombectomy candidate, provide a notification to a user that the subject is a potential LVO or thrombectomy candidate.

The processing circuitry may be further configured to display a first image of an eye region of the subject rendered from the first medical imaging data and/or a second image of the eye region of the subject rendered from the second medical imaging data.

The processing circuitry may be further configured to process the first medical imaging data and/or the second medical imaging data to obtain at least one image feature; and the identifying of whether the subject is a potential LVO or thrombectomy candidate may be further in dependence on the at least one image feature.

The at least one image feature may comprise at least one of: a non-contrast image feature, dense vessel, a hyperdense artery sign (HAS), a susceptibility vessel sign (SVS).

The processing circuitry may be further configured to display at least one image showing an anatomical region comprising the at least one image feature, wherein the at least one image is rendered from the first medical imaging data and/or the second medical imaging data.

The processing circuitry may be further configured to select and display at least one image for review by a user, wherein the at least one image is selected to allow human recognition of an occlusion.

The at least one image for review may comprise a plurality of computed tomography angiography (CTA) views.

The at least one image for review may comprise a plurality of stroke views.

The processing circuitry may be further configured to display to the user a plurality of criteria for LVO/thrombectomy.

The processing circuitry may be further configured to automatically determine whether the subject meets at least some of the plurality of criteria, and to display an indication to the user of whether the subject meets each of the criteria.

The processing circuitry may be further configured to prioritize a workflow in dependence on the identifying of sustained eye gaze deviation and/or in dependence on other information obtained by processing the first medical imaging data and/or second medical imaging data.

Providing the notification may comprise transmitting the notification to a mobile device, for example a smartphone.

The first scan may be a non-contrast CT (NCCT) scan and the second scan may be a contrast CT scan. The first scan may be a NCCT scan and the second scan may be a NCCT scan. The first scan may be an MRI scan and the second scan may be an MRI scan. The first scan may be an optical imaging procedure and the second scan may be a CT scan or MRI scan. The first scan may be a video imaging procedure and the second scan may be a CT scan or MRI scan.

The processing circuitry may be further configured to determine to automatically process the first medical imaging data and/or the second medical imaging data to detect LVO. The identifying of whether the subject is a potential LVO or thrombectomy candidate may be in dependence on the detecting of LVO.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An image display apparatus, comprising:
    processing circuitry configured to receive medical image data of a subject obtained from scanning the subject with one of a CT (Computed Tomography) scanner, a cone-beam CT scanner, an MRI (Magnetic Resonance Imaging) scanner, an X-ray scanner, an ultrasound scanner, a PET (Positron Emission Tomography) scanner, or a SPECT (Single Photon Emission Computed Tomography) scanner, wherein the medical image data includes a representation of at least one eye of the subject, wherein the medical image data comprises at least one of two-dimensional brain scan data or three-dimensional brain scan data; and
    eye gaze detection circuitry configured to process the medical image data to determine whether there is a sustained deviation of an eye gaze direction for the at least one eye of the subject as represented in the medical image data, wherein the processing circuitry is further configured to
        select, from a plurality of display modes, a display mode for displaying the medical image data in dependence on a result of the determination; and
        control a display to display a user interface with user-selectable display elements, and in response to selection of one of the display elements by a user, transform and display the medical image data using the selected display mode, such that the display mode used by the display depends on whether there is a sustained deviation of an eye gaze direction for the at least one eye of the subject as represented in the medical image data, and
    wherein the apparatus further comprises rendering circuitry configured to receive, from the eye gaze detection circuitry, an indication of an eye region of the subject within the medical image data, and render on the display, in the user interface in the selected display mode, at least one image showing the eye region.

2. The apparatus according to claim 1, wherein the deviation of the eye gaze direction is a deviation of eye gaze to a left side or a right side; and
    wherein the processing circuitry is further configured to select a first display mode in response to determining that the sustained deviation of eye gaze direction is present, and select a second, different display mode in response to determining that no sustained deviation of eye gaze direction is present.

3. The apparatus according to claim 1, wherein the medical image data comprises image data acquired for at least two different time points; and
    the processing circuitry is further configured to select the display mode based on the at least two different time points or on an interval between the at least two different time points.

4. The apparatus according to claim 1, wherein the medical image data comprises image data acquired for at least two different time points;
    the processing circuitry is further configured to determine the eye gaze direction by determining a respective eye gaze direction for each of the at least two different time points; and
    the processing circuitry is further configured to select the display mode based on the determined eye gaze direction at the at least two different time points.

5. The apparatus according to claim 4, wherein the processing circuitry is further configured to determine that the sustained deviation of eye gaze is present when determining that a first deviation of eye gaze at a first time point, of the at least two different time points, is consistent with a second deviation of eye gaze at a second time point of the at least two different time points; and
    the processing circuitry is further configured to select a first display mode in response to determining that the sustained deviation of eye gaze direction is present, and select a second, different display mode in response to determining that no sustained deviation of eye gaze direction is present.

6. The apparatus according to claim 1, wherein the processing circuitry is further configured to process the medical image data to detect at least one imaging feature, and select the display mode further in dependence on the detection of the at least one imaging feature.

7. The apparatus according to claim 6, wherein the at least one imaging feature comprises at least one of a dense vessel sign, a hyperdense artery sign, or a susceptibility vessel sign.

8. The apparatus according to claim 6, wherein the medical image data comprises non-contrast scan data, and the at least one imaging feature is detected in the non-contrast scan data.

9. The apparatus according to claim 6, wherein the selected display mode comprises displaying an image including an anatomical region in which the at least one imaging feature is detected.

10. The apparatus according to claim 2, wherein the first display mode comprises displaying a set of computed tomography angiography (CTA) views, and the second display mode comprises displaying a non-contrast computed tomography (NCCT) view.

11. The apparatus according to claim 1, wherein the processing circuitry is further configured to issue a notification to an external device in dependence on the result of the determination.

12. The apparatus according to claim 6, wherein the processing circuitry is further configured to issue a notification to an external device in dependence on the detection of the at least one imaging feature.

13. The apparatus according to claim 1, wherein the processing circuitry is further configured to process the medical image data to detect large vessel occlusion.

14. The apparatus according to claim 1, wherein the processing circuitry is further configured to process the medical image data to render and display an image of an eye region of the subject.

15. The apparatus according to claim 3, wherein the processing circuitry is further configured to:
register image data that is representative of each time point of the at least two different time points;
segment at least one globe of the at least one eye in the image data that is representative of each time point of the at least two different time points; and
display a representation of the segmented at least one globe.

16. The apparatus according to claim 15, wherein the processing circuitry is further configured to segment at least one lens of the at least one eye, and display a representation of the segmented at least one lens, or highlight an eye gaze direction of the segmented at least one globe in the displayed representation.

17. The apparatus according to claim 15, wherein the processing circuitry is further configured to distinguish between representations of different time points of the at least two different time points using different visual effects.

18. The apparatus according to claim 17, wherein at least one of:
the different visual effects used by the processing circuitry comprise different colors used to display the at least one segmented globe;
the different visual effects used by the processing circuitry comprise different line styles used to outline the at least one segmented globe; or
the selected display mode selected by the processing circuitry comprises a display mode in which, in response to an input from the user, fading between the different visual effects is used to compare the representations at the different time points.

19. An apparatus according to claim 15, wherein at least one of:
the selected display mode comprises a display in which a geometry of the at least one eye is morphed between representations at the at least two different time points;
the selected display mode comprises a display in which, in response to an input from the user, an image of the at least one eye is cycled between representations of the at least two different time points; or
the processing circuitry is further configured to render and store a video of an image cycling between representations of the at least two different time points.

20. The image display apparatus of claim 1, wherein the processing circuitry is further configured to segment two eye regions, each containing an eye, included in the medical image data to detect corresponding eye gaze directions of the two eyes.

21. The image display apparatus of claim 1, wherein the medical image data received by the processing circuitry contains information indicating a condition of vessels of the subject.

22. The image display apparatus of claim 1, wherein, in at least one of the plurality of display modes, the processing circuitry is configured to display information relevant for review of a potential thrombectomy candidate.

23. The apparatus according to claim 1, wherein the processing circuitry is further configured to determine, from the medical image data, at least one anatomical region in which at least one imaging feature is present, wherein the presence of the at least one imaging feature is indicative that an occlusion is present and the imaging feature comprises at least one of a dense vessel sign, a hyperdense artery sign, or a susceptibility vessel sign,
the rendering circuitry is further configured to render, on the display in the selected display mode, at least one image showing the determined anatomical region, and
the selection of the display mode and the rendering on the display of the at least one image showing the eye region and at least one image showing the determined anatomical region indicates that the subject is a large vessel occlusion (LVO) or thrombectomy candidate.

24. A method, comprising:
receiving medical image data of a subject obtained from scanning the subject with one of a CT (Computed Tomography) scanner, a cone-beam CT scanner, an MRI (Magnetic Resonance Imaging) scanner, an X-ray scanner, an ultrasound scanner, a PET (Positron Emission Tomography) scanner, or a SPECT (Single Photon Emission Computed Tomography) scanner, wherein the medical image data includes a representation of at least one eye of the subject, wherein the medical image data comprises at least one of two-dimensional brain scan data or three-dimensional brain scan data;
receiving, from eye gaze detection circuitry an indication of an eye region of the subject within the medical image data;
processing the medical image data to determine whether there is a sustained deviation of an eye gaze direction for the at least one eye of the subject as represented in the medical image data;
selecting, from a plurality of display modes, a display mode for displaying the medical image data in dependence on the determination;
controlling a display to display a user interface with user-selectable display elements, and in response to selection of one of the display elements by a user, transform and display the medical image data using the selected display mode, such that the display mode used by the display depends on whether there is a sustained deviation of an eye gaze direction for the at least one eye of the subject as represented in the medical image data; and
rendering, on the display in the user interface in the selected display mode, at least one image showing the eye region.

* * * * *